(12) United States Patent
Castor et al.

(10) Patent No.: US 7,037,534 B2
(45) Date of Patent: May 2, 2006

(54) INACTIVATION OF VIRAL INFECTIONS AGENTS BY CHEMILUMINESCENCE ACTIVATED LIGHT-SENSITIVE COMPOUNDS

(75) Inventors: Trevor Castor, Arlington, MA (US); Lisa Bastiani Lallos, Chelmsford, MA (US); Petr O. Ilynskii, Somerville, MA (US)

(73) Assignee: Aphios Corporation, Woburn, MA (US)

( * ) Notice: Subject to any disclaimer, the term of this patent is extended or adjusted under 35 U.S.C. 154(b) by 284 days.

(21) Appl. No.: 10/280,111

(22) Filed: Oct. 24, 2002

(65) Prior Publication Data

US 2004/0029975 A1    Feb. 12, 2004

Related U.S. Application Data

(60) Provisional application No. 60/334,992, filed on Oct. 24, 2001.

(51) Int. Cl.
*A01N 65/00*    (2006.01)

(52) U.S. Cl. ............... 424/730; 424/94.1; 424/94.6; 424/450; 435/239; 514/449

(58) Field of Classification Search ............... 424/94.1, 424/94.6, 730, 450; 435/238; 514/449
See application file for complete search history.

(56) References Cited

U.S. PATENT DOCUMENTS

| | | | |
|---|---|---|---|
| 4,898,891 A | | 2/1990 | Lavie et al. |
| 5,004,565 A | * | 4/1991 | Schaap ............... 252/7 |
| 5,047,435 A | | 9/1991 | Lavie et al. |
| 5,506,271 A | | 4/1996 | Meruelo et al. |
| 5,780,287 A | * | 7/1998 | Kraus et al. ............ 435/236 |
| 5,786,198 A | | 7/1998 | Kraus et al. |
| 5,952,311 A | * | 9/1999 | Kraus et al. ............ 514/44 |
| 6,160,024 A | | 12/2000 | Kraus et al. |
| 6,245,362 B1 | | 6/2001 | Elten et al. |
| 6,576,784 B1 | | 6/2003 | Mazur et al. |

OTHER PUBLICATIONS

Meruelo, D., G. Lavie and D. Lavie. 1988. Therapeutic Agents with Dramatic Antiretroviral Activity and Little Toxicity at Effective Doses: Aromatic Polycyclic Diones Hypericin and Pseudohypericin. Proc. Natl. Acad. Sci. USA 85:5230-5234.
Lavie, G., F. Valentine, B. Levin, Y. Mazur, G. Gallo, D. Lavie, D. Weiner, and D. Meruelo. 1989. Studies of the Mechanisms of Action of the Antiretroviral Agents Hypericin and Pseudohypericin. Proc. Natl. Acad. Sci. USA 86:5963-5967.
Kraus, G.A.,D. Pratt, J. Tossberg and S. Carpenter. 1990. Antiretroviral Activity of Synthetic Hypericin and Related Analogs. Biochem. Biophys. Res. Commun. 172:149-153.
Schinazi, R.F., C.K. Chu, J.R. Babu, B.J. Oswald, V. Saalmann, D.L. Cannon, B.F. Eriksson, and M. Nasr. 1990. Anthraquinones as a New Class of Antiviral Agents Against Human Immunodeficiency Virus. Antiviral Res. 13:265-272.
Tang, J., J.M. Colacino, S.H. Larsen and W. Spitzer. 1990. Virucidal Activity of Hypericin Against Enveloped and Non-Enveloped DNA and RNA Viruses. Antiviral. Res. 13:313-325.
Carpenter, S. and G.A. Kraus. 1991. Photo sensitization is Required for Inactivation of Equine Infectious Anemia Virus By Hypericin. Photochem Photobiol. 53(2):169-174.
Hudson, J.B., I. Lopez-Bazzocchi and G.H. Towers. 1991. Antiviral Activities of Hypericin. Antiviral. Res. 15:101-112.
Lopez-Bazzocchi I., J.B. Hudson and G.H. Towers. 1991. Antiviral Activity of Photoactive Plant Pigment Hypericin. Photochem. Photobiol. 54:95-98.
Hudson, J.B., P.R. Harris and G.H. Towers, 1993. The Importance of Light in the Anti-HIV Effect of Hypericin. Antiviral. Res. 20:173-178.
Lenard, J., A. Rabson and R. Vanderoef. 1993. Photodynamic Inactivation of Infectivity of Human Immunodeficiency Virus and Other Enveloped Viruses Using Hypericin and Rose Bengal: Inhibition of Fusion and Syncytia Formation. Proc. Natl. Sci. USA 90: 158-162.
Moraleda, G., T.T. Wu, A.R. Jilbert, C.E. Aldrich, L.D. Condreay, S.H. Larsen, J.C. Tang, J.M. Colacino, and W.S. Mason. 1993. Inhibition of Duck Hepatitis B Virus Replication By Hypericin. Antiviral Research 20(3):235-247.
Stevenson, N.R., and J. Lenard. 1993. Antiretroviral Activities of Hypericin and Rose Bengal: Photodynamic Effects on Friend Leukemia Virus Infection of Mice. Antiviral. Res. 21:119-127.
Carpenter, S., M.J. Fehr, G.A. Draus, and J.W. Petrich. 1994 Chemiluminescent Activation of the Antiviral Activity of Hypericin: A Molecular Elashlight. Proc. Natl. Acad. Sci. 91:12273-12277.

(Continued)

Primary Examiner—Leon B. Lankford, Jr.
(74) Attorney, Agent, or Firm—Stephen J. Gaudet; Janine M. Susan (57) ABSTRACT

Described herein is an invention that relates to chemiluminescence-directed antiviral activities of natural and synthesized light-sensitive compounds. Methods are described herein for inactivating infectious virus particles outside and inside an organism. These methods incorporate coupling the antiviral activity of various light-sensitive compounds with chemiluminescence directed by native as well as foreign enzymes of the organism and enhanced by the addition of various anti-quenchers and wavelength-shifting compounds. The methods described herein feature light-sensitive compounds with known antiviral activity exhibited in the presence of light.

14 Claims, 6 Drawing Sheets

OTHER PUBLICATIONS

Gulick, R.M., V. McAuliffe, J. Holden-Wiltse, C. Crumpacker, L. Liebes, D.S. Stein, P. Meehan, S. Hussey, J. Forcht, and F.T. Valentine. 1999. Phase I Studies of Hypericin, the Active Compound in St. John's Wort, as an Antiretroviral Agent in HIV-Infected Adults. AIDS clinical trilas group protocols 150 and 258. Ann. Intern. Med. 130:510-514.

Jacobson, J.M., L. Feinman, L. Liebes, N. Ostrow, V. Koslowski, A. Tobia, B.E. Cabana, D.H. Lee, J. Spritzler, and A.M. Prince. 2001. Pharmacokinetics, Safety, and Antiviral Effects of Hypericin, a Derivative of St. John's Wort Plant, in Patients with Chronic Hepatis C. Virus Infection. Antimicrobial Agents and Chemotherapy 45(2): 517-524.

Wen, J., P. Chowdhury, N.J. Wills, Y. Wannemuehler, J. Park, S. Kesavan, S. Carpenter, G.A. Kraus, and J.W. Pertrich. 2002. Toward the Molecular Flashlight: Preparation, Properties, and Photophysics of a Hypericin-Luciferin Tethered Molecule. Photochem Photobiol 76(2):153-157.

* cited by examiner

INACTIVATION OF VIRAL INFECTIONS AGENTS BY CHEMILUMINESCENCE ACTIVATED LIGHT-SENSITIVE COMPOUNDS

RELATED APPLICATIONS

This application claims priority to Provisional Application Ser. No. 60/334,992, filed Oct. 24, 2001.

FIELD OF INVENTION

The present invention relates to chemiluminescence-directed antiviral activities of natural and synthesized light-sensitive compounds. Specifically, the invention herein describes methods for inactivating infectious virus particles outside and inside an organism, in the latter case being used as a treatment for viral diseases.

BACKGROUND OF THE INVENTION

The development of new antiviral agents is an important and difficult task. In general, compared to other classes of anti-infectives, there are fewer drugs available in the field of antiviral therapy. This is due primarily to features characteristic of viral replication, which occur inside the infected cell and utilizes the cells' molecular machinery. Therefore, there are very few strategies of therapeutic intervention available that do not affect normal cells while simultaneously hindering viral infection. In addition, viral strains resistant to therapy are rapidly emerging, making the available arsenal of drugs significantly less efficient. Some widespread viral diseases (such as hepatitis C, hemorrhagic fever induced by flaviviruses Ebola, Lassa and related viruses) are virtually untreatable. Moreover, a number of new and emerging viral agents refractory to conventional treatment (such as HIV, West Nile encephalitis, hantavirus) have entered the population in recent decades and this trend is likely to continue. Therefore, antiviral agents against one or several viruses would be of immense import to the medical community.

The situation that exists in the field of HIV-induced acquired immunodeficiency syndrome (AIDS) is best known and well publicized. This epidemic started approximately twenty years ago. Currently, there are 36.1 million AIDS cases worldwide with an estimated 5.3 million new HIV infections being reported in the year 2000; the majority of infected individuals reside in the Third World. AIDS, if left untreated, will lead to the death of over 95% of infected individuals within 10 years post-infection.

There is currently no effective vaccine against HIV, notwithstanding concerted scientific and political efforts. Unfortunately, even in the best-case scenario, the generation of a safe and effective HIV vaccine along with its delivery to the population will take at least several years. Further, the most efficient vaccine will not eliminate infection from millions of affected individuals, which will need to rely on various modes of HIV treatment. Therefore, the development of any novel and cost-effective HIV drug will have enormous medical and political significance.

The only major positive development in this field has been a recent formulation of triple-drug therapy, in which patients receive a combination of three different drugs targeting either reverse transcriptase or protease. Earlier modes of monotherapy did not contain the virus for any significant period of time, resulting in the rapid generation of drug-resistant strains and ultimate disease progression. In triple-drug therapy, the virus' proclivity toward mutation is attenuated since drug-induced evolutionary pressure is applied to three different regions of the virus. Thus, these changes are not selected as rapidly (if at all) as in the case when only one drug is administered.

However, while somewhat successful, triple-drug therapy is not without limitations. First, it requires that patients thoroughly follow the drug regimen and are totally compliant therewith. Even a short discontinuation of therapy might result in virus re-emergence. Second, a patients' quality of life is impaired due to various drug-related toxic side effects. And, perhaps most importantly, the cost of these necessary drugs makes them virtually unavailable to the majority of infected individuals (including those outside of health insurance nets of the industrialized world), despite recent political efforts to the contrary. Those efforts, even if they ultimately result in a dramatic slashing of drug prices, will not be able to overturn the tide of the present epidemic, since in the foreseeable future the state of public health systems in the Third World will not provide thorough AIDS diagnostics, drug distribution and monitoring of patients' compliance.

Currently, there are no drugs effective against multiple viral agents. There is an immediate need for a class of therapeutics that can effectively eliminate virulent viruses while at the same time not exerting a toxic profile as to render them unusable.

SUMMARY

This invention relates to the use of chemiluminescence-directed antiviral activities of natural and synthesized light-sensitive compounds in combating viral infections. This invention incorporates coupling the antiviral activity of various light-sensitive compounds with chemiluminescence directed by native and/or foreign enzymes of an organism, and enhanced by the addition of various anti-quenchers and wavelength-shifting compounds. This invention incorporates methods for inactivating infectious virus particles outside and inside an organism, in the latter case being used as a treatment for viral diseases. The methods described herein also relate to the treatment of animals and livestock. The methods presented feature light-sensitive compounds with known antiviral activity exhibited in the presence of light, chemiluminescent substrates susceptible to enzymes that are normally present in tissues or that can be delivered into the organism, and anti-quenchers, substances that dramatically increase luminescence efficacy and that will shift the chemiluminescent compound into the desired wavelength region for action on the light-sensitive compound.

In one embodiment of the present invention, the combined use of hypericin, a light-emitting substrate, and an emission enhancer and light-generating enzyme to achieve significant inactivation of enveloped viruses such as HIV-1 is described. In one aspect of the invention, the use of an enzyme normally present inside an organism, namely, alkaline phosphatase is described. The use of highly active light-emitting substrates, which provide for long and sustained light emission are described in this embodiment. In a particular aspect of this embodiment, the use of emission enhancers, which provide for (1) a specific wavelength peak of emission and (2) possess an anti-quencher effect thus dramatically lengthening chemiluminescence is described.

One embodiment of the instant invention pertains to the encapsulation of the highly stable compounds alluded to above as an antiviral pharmaceutical. In alternative embodiments, the invention addresses the separate encapsulation of the enzyme or an enzyme-encoding plasmid for more efficient delivery and even the use of resident cellular enzymes in order to induce low-level luminescence (in conjunction with an hypericin-substrate-enhancer complex), which is toxic for viruses but not for endogenous cells. The method described in this embodiment is also effective in killing extra-cellular viruses by any luminescence-inducing secreted protein in concert with hypericin or a chemically related compound.

DETAILED DESCRIPTION

The present invention relates to chemiluminescence-directed antiviral activities of natural and synthesized light-sensitive compounds. The methods described herein couple the antiviral activity of various light-sensitive compounds with chemiluminescence catalyzed by native and/or foreign enzymes of an organism, and enhanced by the addition of various anti-quenchers and wavelength-shifting compounds. The methods of the present invention feature light-sensitive compounds with known antiviral activity exhibited in the presence of light, and chemiluminescent substrates susceptible to enzymes that are normally present in cells together with anti-quenchers (i.e., substances that dramatically increase luminescence efficacy and that will shift the chemiluminescent compound into the desired wavelength region for action on the light-sensitive compound). Additionally these substances can be delivered into an organism.

Currently, there are no drugs effective against multiple viral agents. It is important to note that several compounds with broad antiviral activity have been described in the literature, but none of them have attracted substantial attention due to their inherent negative qualities, not the least of which is their toxicity profile making them unsuitable for commercial development. However, there is one class of compounds that do not produce significant toxicity while at the same time containing strong antiviral activity. All of these compounds require light to exert their virucidal activity. These compounds include the light-sensitive plant pigment hypericin and other chemically related compounds.

Hypericin (and related compounds such as pseudohypericin, hypocrellin, etc. and chemical analogs thereof that demonstrate similar virucidal activity as the parent compound) is able to efficiently kill various enveloped viruses (including but not limited to HIV) in the presence of light ranging from about 525 nm to about 600 nm. The mechanism of this process remains enigmatic, however, not wishing to be bound by theory, it likely includes the induction of singlet oxygen atoms together with cross-linking of envelope and capsid proteins of the virus. This wide-ranging antiviral activity has observed in vitro using hypericin concentrations (from about 2 to about 20 µM) that are not toxic for normal animal cells, including human cells.

This phenomenon of hypericin-induced viral inactivation operates even at low concentrations of hypericin, for example, 2 µM, as well as other anthraquinone compounds from plants such as *Hypericum perforatum, Measa perlarius, Stringa asiatica, Drosera rotundifolia* and alike. Importantly, these compounds inactivate most enveloped viruses, including HIV in the absence of significant in vitro cytotoxicity. Cytotoxicity is measured as a function of percent viable cells after incubation with hypericin (or another compound of the present invention) for a defined amount of time. Apart from inherent phototoxicity, which is neutralized when hypericin is light activated, the benign toxicity profile reported is expected for hypericin since it is a major component in St. John's Wort and is being used in other medicinal applications and to date, there have been no reports of any significant toxicity. Hypericin-containing preparations have been rigorously tested, and some have been approved for Investigational New Drug (IND) use by the FDA. Unfortunately, the in vivo therapeutic use of hypericin for antiviral treatment has been precluded by the major requirement for its action, i.e., exposure to visible light, which is impractical within a living organism.

The efficiency (i.e., the elimination of >85% active virus) of hypericin-induced light-mediated viral inactivation is so high that even relatively short exposure times, occurring during routine tissue culture infection procedures, were sufficient for nearly complete, i.e., >90%, inactivation of the exposed virus, notably HIV and other retroviruses. The appreciation of this light exposure requirement has lead to the understanding that fluorescent light provides an even higher degree of hypericin antiviral activity than visible light, rendering non-infective over $10^6$ TCID$_{50}$ (>99.99%) of HIV. Fluorescent light has a wavelength range that is more closely identical to hypericin's optimal absorbance range (i.e., the range where the absorbance of hypericin is maxium) for antiviral activity of 525–600 nm than visible light. Visible light has a broad wavelength range (380–750 nm), while the wavelength range for fluorescent light is narrower. On the contrary, if the virus is treated with hypericin in complete darkness, then the virucidal effects are minimal, if at all detectable. Obviously, one should not expect any benefits from hypericin administration to patients afflicted by viral diseases since there is no ambient light within the cells of the body save those that receive direct exposure. Despite this reasonable assumption, pilot studies of hypericin's benefits for HIV and hepatitis C-infected individuals have been performed with the predictable negative results. The main reason for conducting these trials was hypericin's extremely high antiviral activity in vitro and its advantageous safety profile. At the same time, hypericin has been tested for light-induced inactivation of viruses in blood-related products and this technology has attained a high degree of efficiency.

It has been observed that chemiluminescence, which serves as an alternative source of light emission, can activate hypericin independently of visible light. However, the application of this concept using a luciferase/luciferin system did not effect the desired results. The overall level of virus killing was extremely small and no antiviral effect was demonstrated in the infected cells. There are probably several reasons for this failure including low intensity of luciferin emission, its extremely short time span, the quenching of its emission by water in the body, luciferase stability as well as other factors.

Novel chemiluminescent compounds and systems including secreted alkaline phosphatase (SEAP), which is stronger and more stable than luciferase, various advanced light-emission substrates and emission enhancers were not used in the above-mentioned studies (anti-quenchers were used in the above-mentioned studies). These novel compounds are routinely used in gene reporter systems and are harmless for in vitro cells in cultures. Moreover, secreted alkaline phosphatase is representative of a group of enzymes that are present in normal tissues, i.e., the phosphatases. Therefore, the use of a foreign enzyme for the endogenous induction of alkaline phosphatase-dependent chemiluminescence is not necessary.

One embodiment of the present invention describes a method that employs hypericin, a light-emitting substrate, an emission enhancer and light-generating enzyme in order to inactivate enveloped viruses such as HIV-1. A particular feature of this invention is the use of an enzyme normally present within the organism, alkaline phosphatase, as well as related enzyme activities such as other phosphatases found within the organism. Also included herein are those enzyme activities in which their protein structure has been modified by chemical groups, truncated versions of a parent protein still demonstrating phosphatase activity. Alternatively, such enzymes may be delivered into the organism in the form of protein or DNA by means well known to those in the art.

Another feature of the present invention is the use of highly active light-emitting substrates, which provide for long and sustained light emission. Such light-emitting substrates include water soluble 1,2 dioxetanes like CSPD (disodium 3-(4-methoxyspiro[1,2-dioxetane-3,2'-(5'-chloro)-tricyclo[$3.3.11_{3.7}$]decan]-4-yl)phenyl phosphate) or CDP-STAR (disodium 2 chloro-5-(4-methoxyspiro[1,2-dioxetane-3,2'-(5'-chloro)-tricyclo[$3.3.1.1_{3.7}$]decan]-4-yl)-1-phenyl phosphate), both CSPD and CDP-STAR are available from Applied Biosystems. Included within the scope of this invention are chemical analogs (or modified species) of the light-emitting substrates articulated above given that they retain the light-emitting characteristic of the parent compound.

Emission enhancers provide for a specific wavelength peak of the emission and possess an anti-quencher effect, thus dramatically lengthening chemiluminescence. Emission enhancers of the present invention include quaternary ammonium homopolymers and fluorescent organic compounds like Emerald-II (poly(benzyltributyl)ammonium chloride and sodium fluorescein) from Applied Biosystems. Quaternary ammonium homopolymers like Sapphire-II (poly(benzyltributyl)ammonium chloride) from Applied Biosystems is also an enhancer that can be employed. Additionally, Ruby from Applied Biosystems can be employed as an enhancer. Envisaged to be within the scope of this invention are chemical analogs or otherwise modified versions of emission enhancers mentioned herein provided they retain the emission enhancing characteristic of the parent compound.

In one embodiment, a method for inactivating an enveloped virus is described. In this embodiment an admixture is formed by combining an antiviral light sensitive compound with an enzyme involved in the catalysis of a chemiluminescence substrate, and a chemiluminescence enhancer. In this embodiment, the antiviral light sensitive compound includes, but is not limited to, hypericin, pseudohypericin, hypocrellin and chemically related substances. Chemically related substances can include those chemically modified compounds that retain the antiviral property of their respective parent compound. A chemically related substance can include conjugated constructs in which the parent or a modified version thereof is conjugated with another molecule including a protein, peptide, nucleic acid, carbohydrate, lipid or combinations thereof.

Enzymes of the present embodiment include alkaline phosphatase and its analogs. Analogs can include a truncated version of the protein in which said truncated version retains the enzyme activity of its parent. The retained activity can be greater or lesser when compared to the parent's activity. Other enzymes of the present invention include those capable of catalyzing chemiluminescent substrates. Enzymes included in this category are alkaline phosphatase and other naturally occurring phosphatases residing within the cytoplasm.

Chemiluminescent substrates of the present embodiment include, but are not limited to CSPD or CDP-STAR. Also included are modified substrates having the chemiluminescent ability of the parent compound.

Enhancers of chemiluminescence of the present embodiment are those substances that will prolong the time and efficiency of light emission from the converted chemiluminescent substrate. The enhancers will also shift the wavelength of the resulting interaction between hypericin and the chemiluminescent substrate into the hypericin-preferred part of the spectrum (from about 520 to about 600 nm).

A viral preparation is contacted by the admixture of the present embodiment under conditions suitable for viral inactivation. This viral preparation includes virally infected cells of an intact animal or alternatively, cells contained within a cell culture system. The viral preparation can also include systems in which the virus remains outside a target cell.

An example of extracellular inactivation of a virus includes incubating about 50 $TCID_{50}$ of virus with about 5 µmol of hypericin, about 0.18 units of alkaline phosphatase and about 2.5 mmol of CDP chemiluminescent substrate with an enhancer in a physiological buffer (e.g., phosphate buffered saline, PBS) for approximately two hours at 37° C.

The extracellular procedure can be compared with the intracellular inactivation of a virus that includes incubating acutely infected cells with about 5 µmol of hypericin, about 0.18 units of alkaline phosphatase and about 62.5 µmole of CDP chemiluminescent substrate in a physiological buffer (e.g., PBS) for approximately seven days at 37° C.

One embodiment of the instant invention pertains to the encapsulation of the highly stable compounds alluded to above as an antiviral pharmaceutical according to methods well known in the art. These compounds, including an antiviral light sensitive compound, an enhancer and enzyme, can be encapsulated in pharmaceutical delivery vehicles known in the art. In an alternative aspect of this embodiment, an enzyme-encoding plasmid is introduced into the cells of a cell culture or organism employing known techniques in the art in order to obtain an efficient delivery system for the enzyme. Alternatively, the use of resident (or endogenous) cellular enzymes can be utilized in order to induce low-level luminescence (in conjunction with an hypericin-substrate-enhancer complex), which is toxic for viruses but not for endogenous cells. The methods described in this embodiment are also effective in killing extra-cellular viruses by any luminescence-inducing secreted protein in concert with hypericin or a chemically related compound.

The features and other details of the invention will now be more particularly described and pointed out in the examples. It will be understood that the particular embodiments of the invention are shown by way of illustration and not as limitations of the invention. The principle features of this invention can be employed in various embodiments without departing from the spirit and scope of the invention.

EXAMPLES

Example 1

Inactivation of HIV-1 Replication by Concerted Action of Hypericin and Visible Light HIV-1 Δtat/Δrev stocks were pre-treated with hypericin (5 μmol) and then exposed to visible light (hypericin+light) for 1 hour at 37° C. or kept in the dark for the same amount of time (hypericin+dark). These stocks were then used for infection of CEM-TART cells (CEM cells expressing HIV-1 tat and rev). The data is listed in Table 1 and shown in FIG. 1. Viral stocks exposed to light without hypericin (data not shown) or treated with hypericin in the dark, grew similarly to untreated virus (not shown in FIG. 1). Greater than 99% of the virus was inactivated when exposed to hypericin and light, even after 20 days of culture.

TABLE 1

Inactivation of HIV-1 Replication by Concerted Action of Hypericin and Visible Light

| Amount of HIV used, treated by | HIV p24 concentration (ng/ml) Days Post-infection | | | | | |
|---|---|---|---|---|---|---|
| | 0 | 3 | 7 | 9 | 13 | 17 | 20 |
| 50 $TCID_{50}$, 5 μm hypericin + light | 1 | 0.87 | 1.57 | 8.12 | 2.04 | 2.20 | 6.85 |
| 50 $TCID_{50}$, 5 μm hypericin + dark | 1 | 1.84 | 60.53 | 606.57 | 935.42 | 1000 | 1000.61 |
| 50 $TCID_{50}$ virus only | 1 | 5.96 | 180.35 | 2113.7 | 1659.86 | 1116.11 | 1599.33 |

Figure 1:
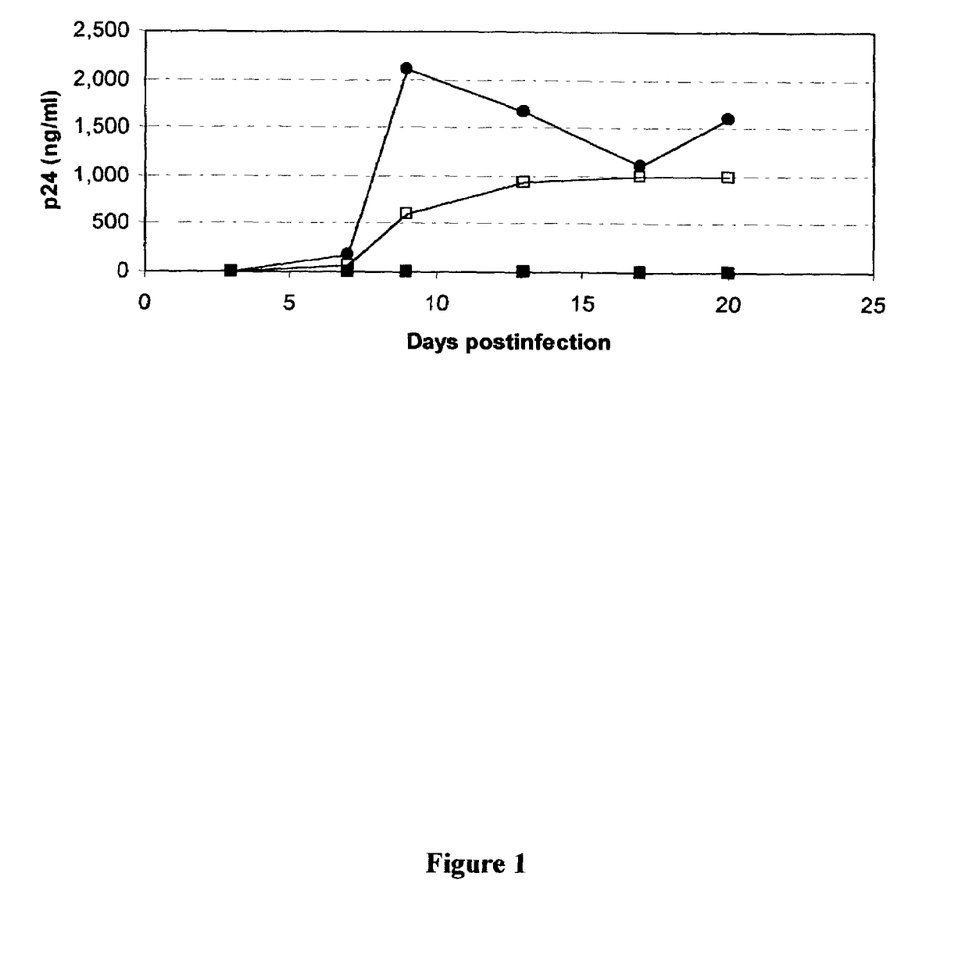
FIG. 1 is a graph illustrating the inactivation of HIV-1 replication by the concerted action of hypericin and visible light.

FIG. 1 illustrates the inactivation of HIV-1 by the concerted action of hypericin and visible light. Infection of CEM-TART cells with HIV-Δtat/Δrev strain was performed for 1 hour with 50 $TCID_{50}$ upon exposure of viral stock to 5 μM of hypericin and visible light (solid squares) or dark (open squares) for 2 hours at 37° C. Untreated virus was also used to infect CEM-TART cells at 50 $TCID_{50}$ (solid circles) after a 2-hour incubation at 37° C. Greater than 99% of the virus was inactivated when exposed to hypericin and light, even after 20 days of culture.

Example 2

Virucidal Effect of Hypericin and Chemiluminescence-Inducing Compounds

Approximately 50 $TCID_{50}$ (1 ng of p24) of HIV-1Δtat/Δrev viral stocks treated with various combinations of hypericin (5 μmol, Hyp), chemiluminescence substrate with enhancer (2.5 mmol) and alkaline phosphatase (0.18 u, AP) for 1 hour at 37° C. were used to infect CEM-TART cells, which were then passaged in a conventional manner (samples taken every 3–4 days before replacing tissue culture media). The contents of each experimental sample are shown in the left column of Table 2. Each mixture was tested in duplicate. HIV replication was measured by the amount of p24 capsid protein in the culture media. Hypericin exposed to light (hyp+light) is a positive control of viral inhibition. Emerald™ enhancer was used. The averaged data of duplicate samples is shown graphically in FIG. 2. Incubating virus with hypericin, alkaline phosphatase and a chemiluminescent substrate with enhancer results in equivalent virus inactivation as when hypericin and visible light are used (99.3% virus reduction with chemiluminescent substrate and enhancer versus 99.4% virus reduction with visible light on day 7 post-infection.

TABLE 2

Virucidal Effect of Hypericin and Chemiluminescence-Inducing Compounds

| Mixture components | HIV p24 concentration (ng/ml) Days Post-infection | | | | | |
|---|---|---|---|---|---|---|
| | 0 | 4 | 7 | 11 | 15 | 18 |
| Hyp + Enhancer + AP + dark | 1 | 1.4 | 2.3 | 37 | 12 | 2.8 |
| | 1 | 1.7 | 5.3 | 48 | 15 | 13 |
| Hyp + Enhancer + dark | 1 | 2.5 | 39.5 | 327 | 104 | 11 |
| | 1 | 3.1 | 42 | 195 | 45 | 178 |
| Hyp + AP + dark | 1 | 3.8 | 251 | 5774 | 1506 | 1307 |
| | 1 | 2.7 | 269 | 3088 | 917 | 329 |
| Untreated virus | 1 | 3.3 | 462 | 3838 | 1405 | 766 |
| Hyp + light | 1 | 1 | 4.1 | 44.7 | 11343 | 4011 |
| | 1 | 1 | 1.2 | 2.2 | 1.9 | 1 |

Figure 2:
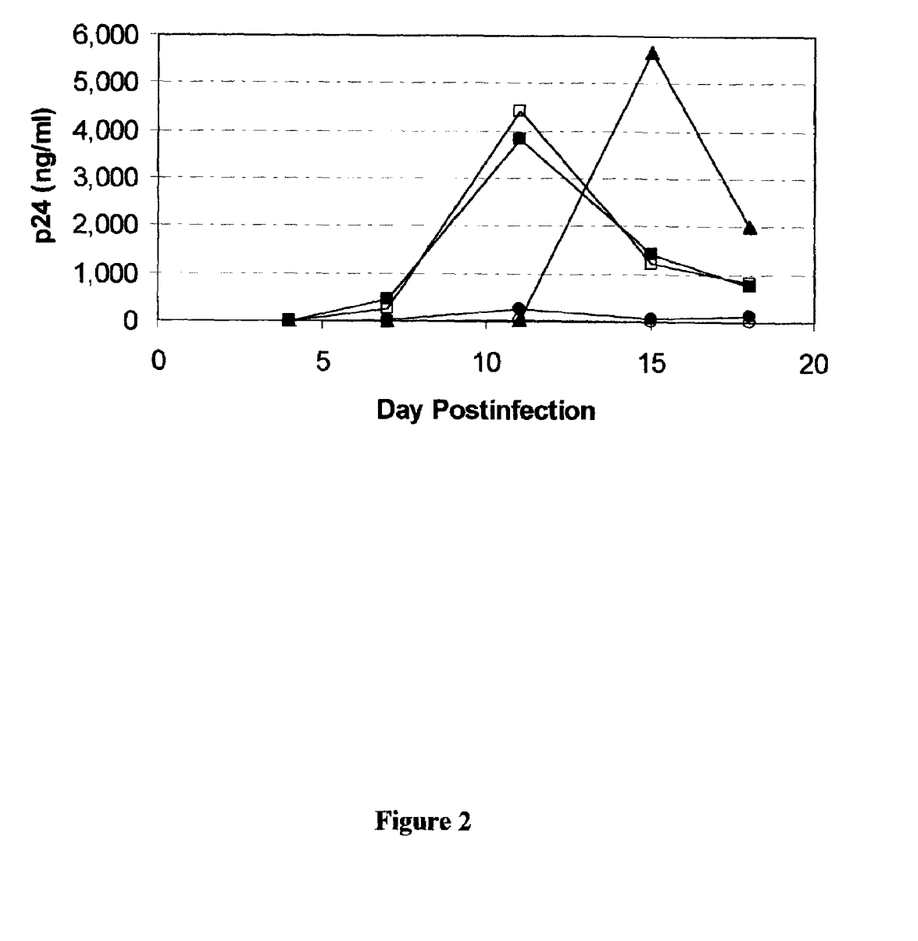
FIG. 2 is a graph showing the virucidal effect of hypericin and some chemiluminescence-inducing compounds such as alkaline phosphatase and CSPD/Emerald.

FIG. 2 illustrates the virucidal effect of hypericin and chemiluminescence-inducing compounds. Approximately 50 $TCID_{50}$ of HIV Δtat/Δrev viral stocks were pre-treated with a mixture of hypericin, chemiluminescence substrate with enhancer and/or alkaline phosphatase (AP) for 1 hour at 37° C. and then used to infect CEM-TART cells. HIV p24 was monitored over time. Data is the average of duplicate samples. Open circles, virus+hypericin+enhancer+AP+dark; solid circles, virus+hypericin+enhancer+dark; open squares, virus+hypericin+AP+dark; solid squares, untreated virus; solid triangles, virus+hypericin+visible light. Data is the average of duplicate samples. Incubating virus with hypericin, alkaline phosphatase and a chemiluminescent substrate with enhancer results in equivalent virus inactivation as when hypericin and visible light are used (99.27% virus reduction with chemiluminescent substrate and enhancer versus 99.4% virus reduction with visible light on day 7 post-infection).

Example 3

Figure 3:
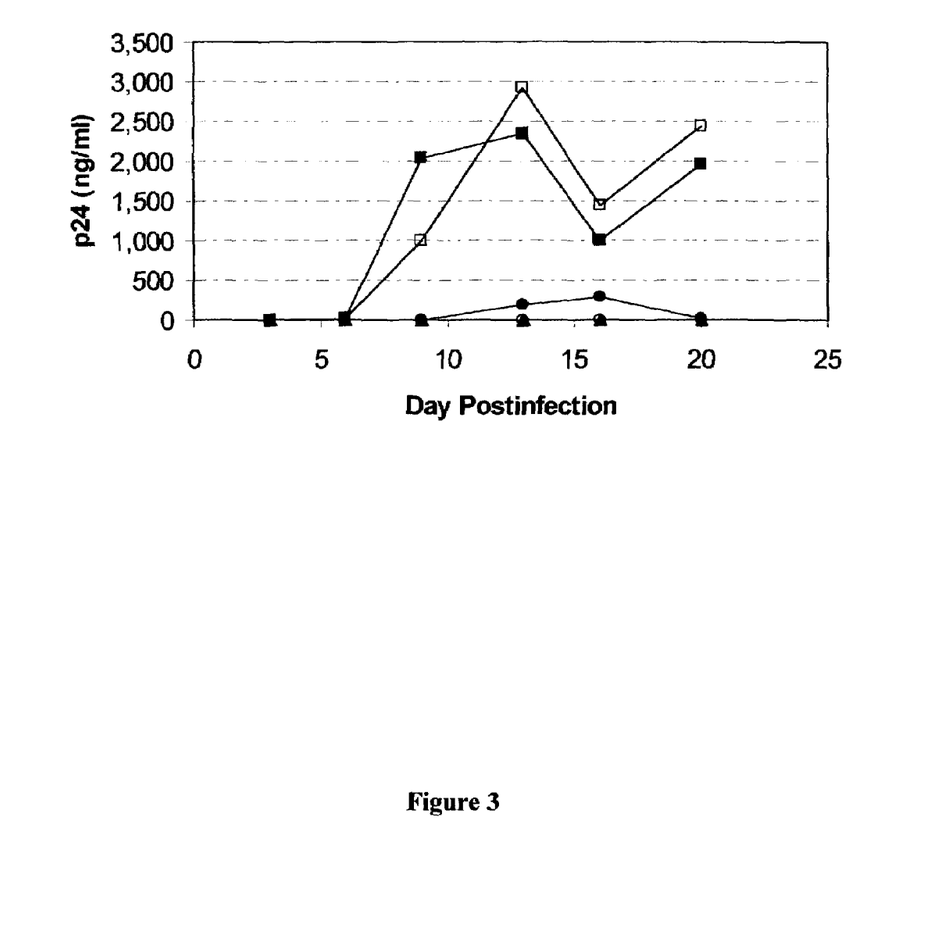
FIG. 3 is a graph depicting the level of virucidal effect of chemiluminescence-induced hypericin action as a function of the concentration of the active enzyme.

The level of Virucidal Effect of Chemiluminescence-Induced Hypericin Action is Dependent on the Concentration of the Luminogenic Enzyme Approximately 50 $TCID_{50}$ (1 ng of p24) of HIV-1Δtat/Δrev viral stocks were pre-treated with a mixture of hypericin (5 μmol Hyp), luminescence substrate with Ruby™ enhancer (Ruby) and different doses of alkaline phosphatase (AP) for 2 hours at 37° C. and then used to infect CEM-TART cells. Cells culture media was exchanged every 3–4 days and samples for p24 analysis were taken at the same time. HIV replication was measured by the amount of p24 capsid protein in the culture media. Samples treated with hypericin and exposed to the light (hyp+light) was a positive control of viral inhibition; unexposed samples (hyp+dark) were used as negative control. Samples were tested in triplicate. The raw data are listed in Table 3 and the averaged data is shown in FIG. 3. Small amounts of alkaline phosphatase are sufficient to catalyze the chemiluminescent substrate in the generation of light for hypericin action.

TABLE 3

The Level of Virucidal Effect of Chemiluminescence-Induced Hypericin Action is Dependent on the Concentration of the Luminogenic Enzyme

| | HIV p24 concentration (ng/ml) Days Post-infection | | | | | | |
|---|---|---|---|---|---|---|---|
| Mixture components | 0 | 3 | 6 | 9 | 13 | 16 | 20 |
| Hyp + Ruby + 0.0075 U AP + dark | 1 | 0.05 | 0.2 | 7.2 | 1.9 | 1.4 | 5.1 |
| | 1 | 0.69 | 1 | 3.5 | 1.9 | 1.3 | 4.3 |
| | 1 | 0.05 | 2 | 10 | 601 | 852 | 29 |
| Hyp + Ruby + 0.18 U AP + dark | 1 | 0.05 | 0.05 | 3.1 | 0.05 | 0.05 | 3.6 |
| | 1 | 0.05 | 0.05 | 3 | 1.85 | 0.05 | 2.6 |
| | 1 | 0.05 | 0.05 | 3.3 | 3.6 | 1.4 | 2.9 |
| Hyp + dark | 1 | 0.05 | 12.13 | 831 | 3,501 | 1543 | 2,789 |
| | 1 | 0.05 | 11 | 1,120 | 3,270 | 923 | 2,775 |
| | 1 | 0.05 | 19.34 | 1,055 | 1,985 | 1,870 | 1,763 |
| Hyp + light | 1 | 0.05 | 0.05 | 3 | 2.9 | 0.05 | 6.6 |
| Untreated virus | 1 | 0.124 | 19.25 | 2,032 | 2,352 | 1,008 | 1,958 |

FIG. 3 illustrates the level of virucidal effect of chemiluminescence-induced hypericin action is dependent on the concentration of the luminogenic enzyme. Approximately 50 $TCID_{50}$ of HIV Δtat/Δrev viral stocks were pre-treated with a mixture of 5 μmol of hypericin, luminescence substrate with Ruby enhancer and/or two different doses of alkaline phosphatase (AP) for 2 hours at 37° C. and then used to infect CEM-TART cells. HIV p24 was monitored over time. Data is the average of triplicate samples. Closed circles, virus+Ruby+0.0075 U AP+dark; open circles, virus+Ruby+0.18 U AP+dark; closed triangles, virus+hypericin+light; open squares, virus+hypercin+dark; closed squares, virus only. Small amounts of alkaline phosphatase are sufficient to catalyze the chemiluminescent substrate in the generation of light for hypericin action.

Example 4

Figure 4:
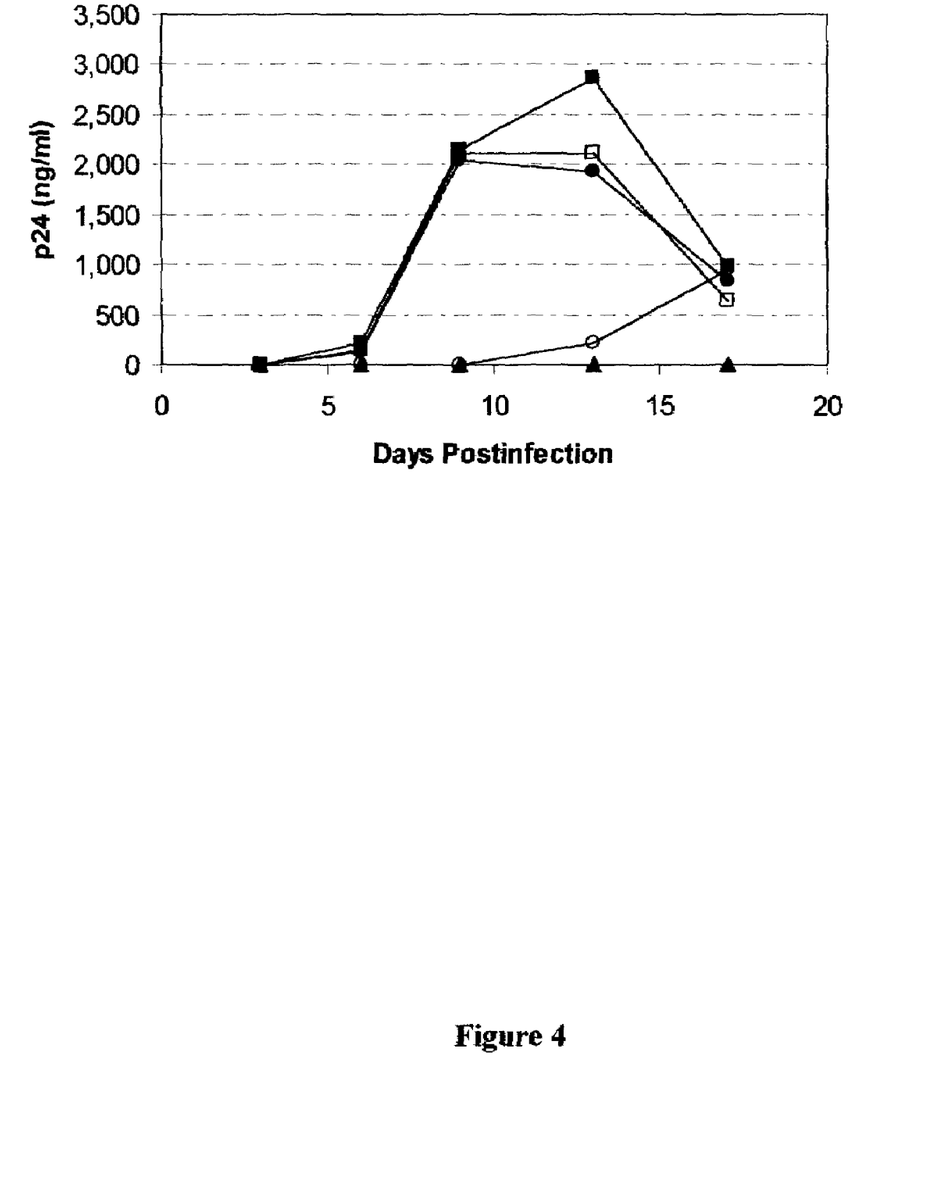
FIG. 4 is a graph depicting the importance of the presence of an enhancer/substrate mixture for the virucidal effect of alkaline phosphatase-induced hypericin action.

Presence of Enhancer/Substrate Mixture is Essential for Virucidal Effect of Alkaline Phosphatase-Induced Hypericin Action Approximately 50 $TCID_{50}$ of HIV-1Δtat/Δrev viral stocks were pre-treated with a mixture of hypericin (5 μmol, Hyp), with or without chemiluminescence substrate pre-mixed with a Ruby™ enhancer (1.25 mmol Ruby), and alkaline phosphatase (0.036 U, AP) for 2 hours at 37° C. and then used to infect CEM-TART cells. HIV replication was measured by the amount of p24 capsid protein in the culture media. Samples treated with hypericin and exposed to the light (Hyp+light) served as a positive control of viral inhibition, unexposed samples (Hyp+dark 1 and 2) were used as negative controls. Samples were tested in duplicate. The raw data are listed in Table 4 and the averaged data is shown in FIG. 4. The presence of the chemiluminescent substrate with enhancer is necessary for the virucidal action of alkaline phosphatase-induced hypericin action.

TABLE 4

Presence of Enhancer/Substrate Mixture is Essential for Virucidal Effect of Alkaline Phosphatase-Induced Hypericin Action

| | HIV p24 concentration (ng/ml) Days Post-infection | | | | | |
|---|---|---|---|---|---|---|
| Mixture components | 0 | 3 | 6 | 9 | 13 | 17 |
| Hyp + AP + Enhancer/Substrate + dark | 1 | 0.05 | 0.05 | 2.8 | 214 | 945.5 |
| | 1 | 0.05 | 0.05 | 6 | 210 | 958.2 |
| Hyp + AP + dark | 1 | 1.4 | 74.4 | 1,908 | 1,925 | 705.4 |
| | 1 | 5.4 | 196 | 2,167 | 1,948 | 958.2 |
| Hyp + dark | 1 | 3.3 | 149 | 2,191 | 2,322 | 662.5 |
| | 1 | 4 | 144 | 2,031 | 1,909 | 609.5 |
| Hyp + light | 1 | 0.05 | 0.05 | 0.05 | 0.05 | 0.05 |
| Untreated virus | 1 | 2.3 | 222 | 2,150 | 2,868 | 976 |

FIG. 4 illustrates that the presence of the enhancer/substrate mixture is essential for virucidal effect of alkaline phosphatase-induced hypericin action. Approximately 50 $TCID_{50}$ of HIV Δtat/Δrev viral stocks were pre-treated with a mixture of 5 μmol of hypericin with or without chemiluminescence substrate with Ruby enhancer and alkaline phosphatase (AP) for 2 hours at 37° C. and then used to infect CEM-TART cells. HIV p24 was monitored over time. Data is the average of duplicate samples. Open circles, virus+hypericin+AP+Enhancer/Substrate+dark; closed circles, virus+hypericin+AP+dark; closed triangle, virus+hypericin+light; open square, virus+hypercin+dark; closed square, virus only. The presence of the chemiluminescent substrate with enhancer is necessary for the virucidal action of alkaline phosphatase-induced hypericin action.

Example 5

Inhibition of HIV-1Δtat/Δrev Growth in Infected Cultures by a Concerted Action of Hypericin, Chemiluminescent Substrate and Alkaline Phosphatase CEM-TART cells infected with 13–20 $TCID_{50}$ of HIV-1Δtat/Δrev were incubated with hypericin (5 μmol), alkaline phosphatase (Calbiochem, 0.18 U) and chemiluminescent substrate CDP-Star in the concentrations shown. Tissue culture media was replaced every 3–4 days. HIV replication was measured by the amount of p24 capsid protein in the culture media from day 7. The median data of three replicates are listed in Table 5 and shown in FIG. 5. Not only can hypericin inactivate extracellular virus, but it can also eliminate virus from infected cells.

TABLE 5

Inhibition of HIV-1Δtat/Δrev Growth in Infected Cultures by a Concerted Action of Hypericin, Chemiluminescent Substrate and Alkaline Phosphatase

| HIV-1 Δtat/Δrev-infected CEM-TART cells treated with: | p24 concentration (ng/ml) on day 7 postinfection |
|---|---|
| Hypericin, alkaline phosphatase, 62.5 μm CDP | 11 |
| Hypericin, 62.5 μm CDP | 110 |
| Hypericin, alkaline phosphatase, 125 μm CDP | 8.8 |
| Hypericin, 125 μm CDP | 100 |
| Untreated virus | 592 |

Figure 5:
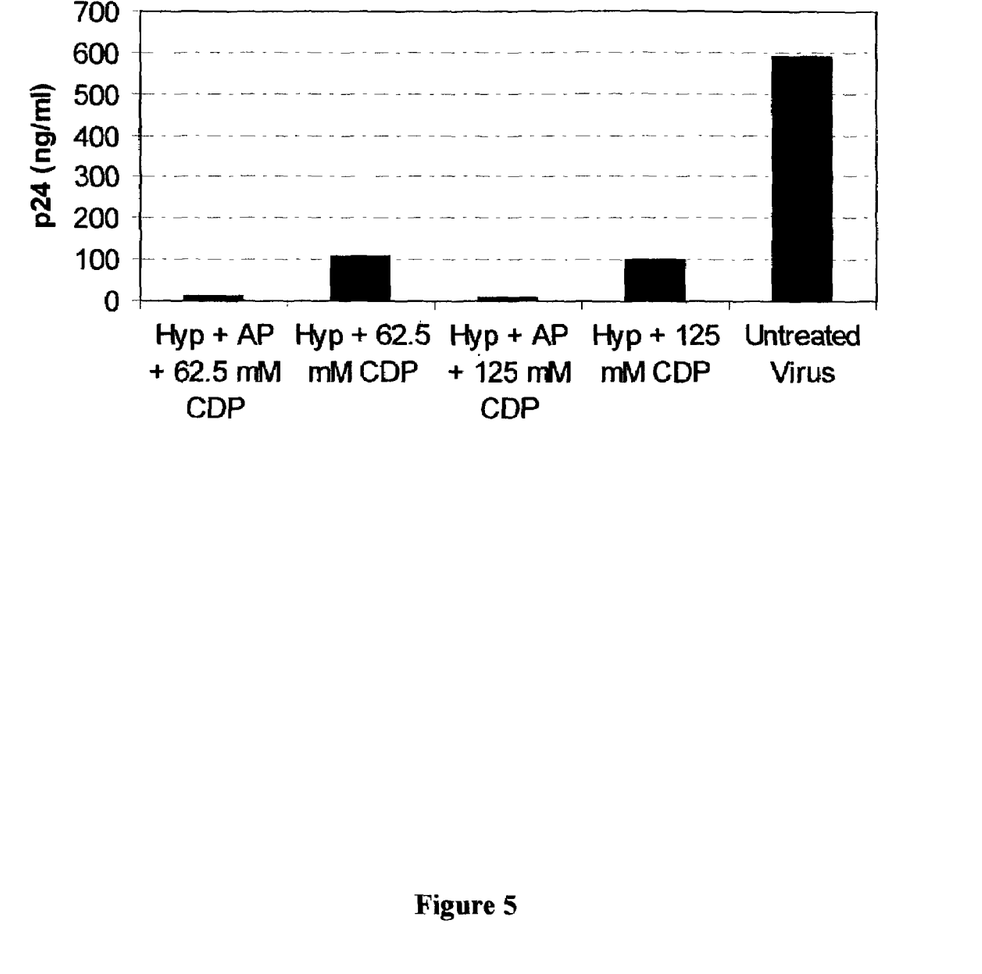
FIG. 5 is a graph showing the inhibition of HIV-1Δtat/Δrev growth in virally infected cultures by the concerted action of hypericin, chemiluminescent substrate and alkaline phosphatase.

FIG. 5 illustrates the inhibition of HIV-1Δtat/Δrev growth in infected cultures by a concerted action of hypericin, chemiluminescent substrate and alkaline phosphatase. CEM-TART cells infected with 13–20 TCID$_{50}$ of HIV-1Δtat/Δrev were incubated with hypericin, alkaline phosphatase and a chemiluminescent substrate. The amount of p24 on day 7 post-infection was determined by ELISA. Data given above is the median of triplicates. Not only can hypericin inactivate extracellular virus, but it can also eliminate virus from infected cells.

Example 6

Inhibition of HIV-1$_{IIIB}$ Growth in Infected Cultures by a Concerted Action of Hypericin, Chemiluminescent Substrate and Alkaline Phosphatase CEM-SS cells were infected with 13–20 TCID$_{50}$ of HIV-1$_{IIIB}$, and then incubated with hypericin (5 μmol), alkaline phosphatase (Calbiochem, 0.18 U) and chemiluminescent substrate CDP in the concentrations shown. Tissue culture media was replaced every 3–4 days. HIV replication was measured by the amount of p24 capsid protein in the culture media from day 7. The median data of three replicates are listed in Table 6 and shown in FIG. 6. The alkaline phosphatase-induced hypericin action is also effective against fully competent virus.

TABLE 6

Inhibition of HIV-1$_{IIIB}$ Growth in Infected Cultures by a Concerted Action of Hypericin, Chemiluminescent Substrate and Alkaline Phosphatase

| HIV-1$_{IIIB}$-infected CEM-SS cells treated with: | p24 concentration (ng/ml) on day 7 post-infection |
|---|---|
| Hyp + AP + 125 μm CDP + dark | 161 |
| Hyp + 125 μm CDP + dark | 664 |
| Hyp + AP + 375 μm CDP + dark | 6 |
| Hyp + 375 μm CDP + dark | 219 |
| Untreated virus | 2766.7 |

Figure 6:
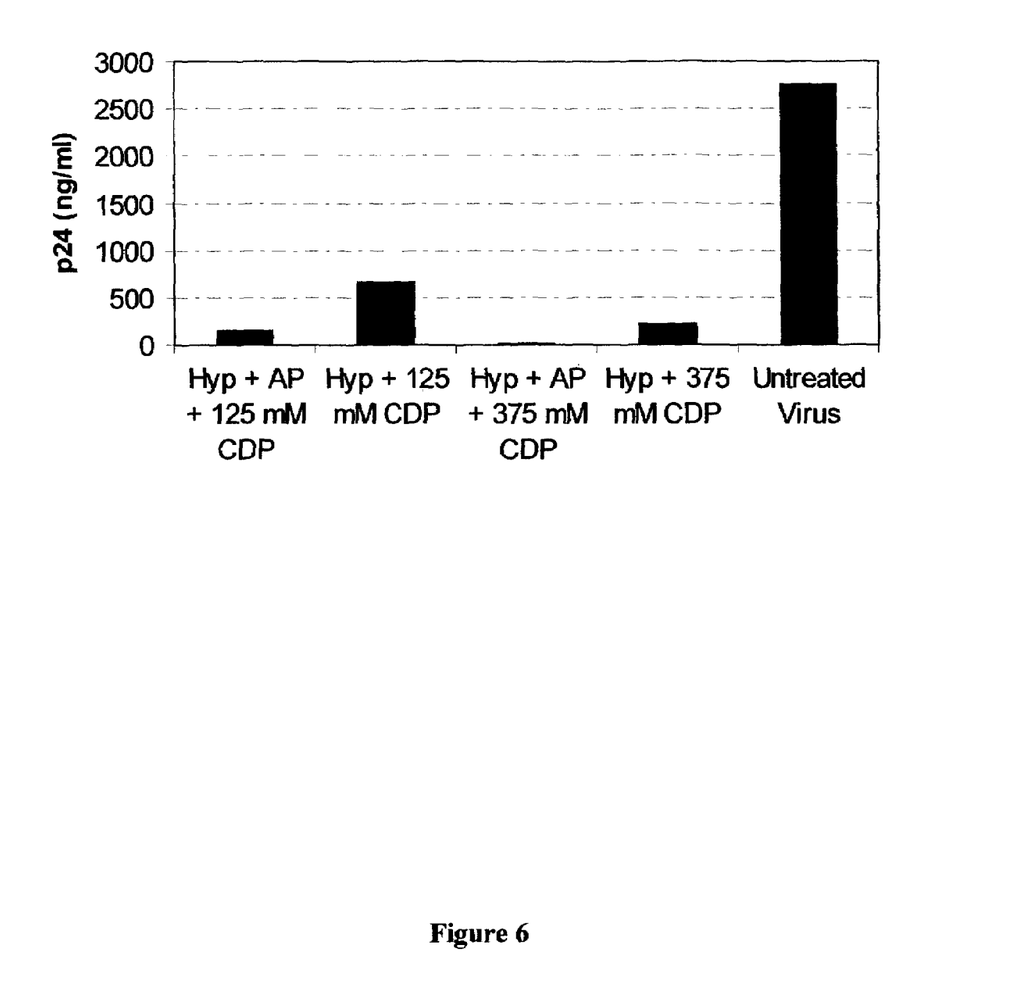
FIG. 6 is a graph showing the inhibition of HIV-1$_{IIIB}$ growth in virally infected cultures by the concerted action of hypericin, chemiluminescent substrate and alkaline phosphatase.

FIG. 6 illustrates the inhibition of HIV-1$_{IIIB}$ growth in infected cultures by a concerted action of hypericin, chemiluminescent substrate and alkaline phosphatase. CEM-SS cells infected with 13–20 TCID$_{50}$ of HIV-1$_{IIIB}$ were incubated with hypericin, alkaline phosphatase and a chemiluminescent substrate. The amount of p24 on day 7 post-infection was determined by ELISA. Data given above is the median of triplicates. The alkaline phosphatase-induced hypericin action is also effective against fully competent virus.

While this invention has been particularly shown and described with reference to embodiments thereof, it will be appreciated by those skilled in the art that various changes in form and detail may be made therein without departing from the spirit and scope of the invention as defined by the appended claims hereto.

The invention claimed is:

1. An antiviral complex, comprising an antiviral light sensitive compound, a phosphatase enzyme, a chemiluminescence substrate, and a chemiluminescence enhancer, wherein said antiviral light sensitive compound is selected from the group consisting of hypericin, pseudohypericin, and hypocrellin; and wherein said chemiluminescence substrate is a water soluble 1,2-dioxetane; and wherein said chemiluminescence enhancer is a quaternary ammonium homopolymer with or without a fluorescent organic compound.

2. The complex of claim 1, wherein said antiviral light sensitive compound is hypericin.

3. The complex of claim 1, wherein said phosphatase enzyme is alkaline phosphatase or an analog thereof.

4. The complex of claim 1, wherein said 1,2-dioxetane is disodium 3-(4-methoxyspiro[1,2-dioxetane-3,2'-(5'-chloro)-tricyclo[3.3.1.1$_{3,7}$]decan]-4-yl)phenyl phosphate (CSPD).

5. The complex of claim 1, wherein said 1,2-dioxetane is disodium 2-chloro-5-(4-methoxyspiro[1,2-dioxetane-3,2'-(5'chloro)-tricyclo[3.3.1.1$_{3,7}$]decan]-4-yl)- 1-phenyl phosphate (CDP-STAR).

6. The complex of claim 1, wherein said chemiluminescence enhancer is poly(benzyltributyl)ammonium chloride (SAPPHIRE-II).

7. The complex of claim 6, wherein said chemiluminescence enhancer is poly(benzyltributyl)ammonium chloride and sodium fluorescein (EMERALD-II).

8. A method of inactivating an enveloped virus, comprising:
(a) forming an admixture having an antiviral light sensitive compound, a phosphatase enzyme, a chemiluminescence substrate, and a chemiluminescence enhancer, wherein said antiviral light sensitive compound is selected from the group consisting of hypericin, pseudohypericin, and hypocrellin; and wherein said chemiluminescence substrate is a water soluble 1,2-dioxetane; and wherein said chemiluminescence enhancer is a quaternary ammonium homopolymer with or without a fluorescent organic compound; and
(b) contacting said enveloped virus with said admixture of (a) under conditions suitable for inactivating said enveloped virus.

9. The method of claim 8, wherein a source of said enveloped virus includes a cell culture with an innoculum of extracellular virus, intracellular virus and a combination thereof.

10. The method of claim 8, wherein a source for said enveloped virus includes an organism infected with said enveloped virus.

11. The method of claim 8, wherein said antiviral light sensitive compound is hypericin.

12. The method of claim 8, wherein said phosphatase enzyme is alkaline phosphatase or an analog thereof.

13. The method of claim 8, wherein said chemiluminescence substrate is selected from the group consisting of disodium 3-(4-methoxyspiro[1,2-dioxetane-3,2'-(5'-chloro)-tricyclo[3.3.1.1$_{3,7}$]decan]-4-yl)phenyl phosphate (CSPD), disodium 2-chloro-5-(4-methoxyspiro[1,2-dioxetane-3,2'-(5chloro)-tricyclo[3.3.1.1$_{3,7}$]decan]-4-yl)-1-phenyl phosphate (CDP-STAR), and chemical modifications thereof.

14. The method of claim 8, wherein said chemiluminescence enhancer is selected from the group consisting of poly(benzyltributyl)ammonium chloride (SAPPHIRE-II), poly(benzyltributyl)ammonium chloride and sodium fluorescein (EMERALD-II), and chemical modifications thereof.

* * * * *